US00PP14307P29

(12) United States Plant Patent
Solari et al.

(10) Patent No.: US PP14,307 P2
(45) Date of Patent: Nov. 18, 2003

(54) PULMONARIA PLANT NAMED 'PINK HAZE'

(50) Latin Name: *Pulmonaria saccharata*
Varietal Denomination: Pink Haze

(76) Inventors: John Ernest Solari, 153 Saunders Lane., Mayford Woking Surrey GU22 0nt (GB); Rosemary Ann Solari, 153 Saunders Lane, Mayford Woking Surrey GU22 0nt (GB)

( * ) Notice: Subject to any disclaimer, the term of this patent is extended or adjusted under 35 U.S.C. 154(b) by 0 days.

(21) Appl. No.: 10/290,883

(22) Filed: Nov. 8, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para

(57) ABSTRACT

A new cultivar of Pulmonaria plant named 'Pink Haze' that is characterized by a low-growing, dense, mounding habit, variegated medium-green leaves with grey-green spots, and bright, large, clear-pink wide open flowers with tints of violet-blue. In combination these traits set 'Pink Haze' apart from all other existing varieties of Pulmonaria known to the inventor.

2 Drawing Sheets

Genus: PULMONARIA.
Species: *saccharata.*
Denomination: PINK HAZE.

BACKGROUND OF THE INVENTION

The present invention relates to a new and distinct cultivar of lungwort that is grown as an ornamental for its large clear-pink flowers. The new cultivar is known botanically as *Pulmonaria saccharata* and will be referred to hereinafter by the cultivar name 'Pink Haze'.

'Pink Haze' is a chance seedling that was discovered in October 1996 by the inventors in a cultivated area in Woking, Surrey, United Kingdom. Surrounding 'Pink Haze' were plants presumed to be *Pulmonaria saccharata*. The female parent is presumed to be *Pulmonaria saccharata* (unpatented). Selection of 'Pink Haze' was based on the clear-pink flower color, the wide open flower, and the size of the flower, which is much larger than exhibited by typical Pulmonaria. 'Pink Haze' is a ground cover suitable for full shade or light shade and exhibiting leaves that are up to 25 centimeters in length and up to 10 centimeters in width on a mature plant. At maturity 'Pink Haze' is 30 centimeters in height and 50 centimeters in width.

'Pink Haze' produces many large wide open, clear-pink flowers shaped like saucers with ruffled edges. There are tints of violet-blue in the flower color. The flowers are held above medium-green leaves that are dappled on the upper surface with grey-green spots. The flowers bloom in early spring. Propagation is accomplished by division or tissue culture. Plants perform best when planted in moist, organically enriched soil. 'Pink Haze' is suitable as a ground cover for woodland paths, perennial beds and small shady landscape areas.

The plant that is closest in comparison to 'Pink Haze' is Pulmonaria 'Dora Bielefeld' (unpatented). 'Pink Haze' is distinguishable from the comparison plant by its flowers, which are approximately twice the size and a clearer, brighter pink color than the flowers of 'Dora Bielefeld'. 'Pink Haze' is distinguishable from the presumed parent and all other Pulmonaria known to the inventor, by its wide open flower, clear-pink flower color and large flowers.

'Pink Haze' was first asexually propagated by the inventors in 1996 in a cultivated area of Woking, Surrey, United Kingdom. The method used for asexual propagation was division. Since that time the characteristics of the new cultivar have been determined stable and are reproduced true to type in successive generations.

SUMMARY OF THE INVENTION

The following traits have been repeatedly observed and represent the distinguishing characteristics of the new cultivar 'Pink Haze'. In combination these traits set 'Pink Haze' apart from all other Pulmonaria known to the inventor. 'Pink Haze' has not been tested under all possible conditions and phenotypic differences may be observed with variations in environmental, climatic and cultural conditions, however, without any variance in genotype.

1. Pulmonaria 'Pink Haze' is a ground cover exhibiting a low-growing, dense, mounding habit.
2. Pulmonaria 'Pink Haze' produces a profuse display of bright clear-pink flowers with tints of violet-blue color.
3. Pulmonaria 'Pink Haze' is a perennial suitable for woodland paths, perennial beds and shady to partially shaded landscape areas.
4. Pulmonaria 'Pink Haze' is 20 cm. in height and 43 cm. in width in a 4-litre container, while 30 cm. in height and 50 cm. in width at maturity.
5. Pulmonaria 'Pink Haze' exhibits variegated medium green foliage with a dappled pattern of grey-green spots on the leaf surfaces.
6. Pulmonaria 'Pink Haze' is hardy to USDA Zone 5.

BRIEF DESCRIPTION OF THE DRAWINGS

The accompanying colored drawings illustrate the overall appearance of the new cultivar 'Pink Haze' showing the colors as true as it is reasonably possible to obtain in colored reproductions of this type. Colors in the photographs may differ from the color values cited in the detailed botanical description, which more accurately describes the actual colors of the new variety 'Pink Haze'.

The drawing on sheet 1 illustrates an entire plant from a side perspective.

The drawing on sheet 2 shows a closer view of the flowers and leaves. All photographs were made using conventional techniques and although colors may appear different from actual colors due to light reflectance they are as accurate as possible by conventional photography.

BOTANICAL DESCRIPTION OF THE PLANT

The following is a detailed description of the new Pulmonaria named 'Pink Haze'. Datum was collected in Arroyo Grande Calif. from 2 year old plants grown in four-litre containers. The color determinations are in accordance with The 2001 Royal Horticultural Society Colour Chart of The Royal Horticultural Society, London, England, except where general color terms of ordinary dictionary significance are used. There are no growing problems known to the inventor.

Botanical classification: Pulmonaria 'Pink Haze'.
Species: *saccharata.*
Commercial classification: Perennial herb.
Common name: Lungwort.
Use: Ornamental groundcover for woodland path, perennial border and small landscape areas.
Cultural requirements: Performs best with regular watering and full or partial shade using organically enriched, moist, well-draining soil.
Parentage: Pulmonaria 'Pink Haze' is a chance seedling that resulted from the open pollination of unidentified female and male parent plants. The exact parents are unidentified but the presumed female parent is *Pulmonaria saccharata.*
Plant description:
- *Bloom period.*—Early spring.
- *Plant habit.*—Low-growing, dense and mounding.
- *Height.*—20 cm. in height from soil level in a 4-litre container.
- *Width.*—43 cm. in width in a 4-litre container.
- *Hardiness.*—USDA Zone 5.
- *Vigour.*—Vigorous.
- *Rooting habit.*—Fibrous and fleshy.
- *Propagation.*—Propagation is accomplished by division and tissue culture.
- *Crop time.*—12 months to produce a 4-litre container size from division.
- *Special growing requirements.*—Keep liners in shade house in late spring and early summer. In fall plant these in 2-litre containers and place in a well ventilated polythene tunnel. Liquid feed in late winter to encourage fresh well-colored foliage and flowers.
- *Disease and pest problems.*—No disease or pest problems known to the inventor.

Stem:
- *Basal stem shape.*—Cylindrical.
- *Stem color.*—144B.
- *Stem dimensions.*—1.50–2.00 cm. in length and 6 mm. in diameter.
- *Stem surface.*—Pubescent.
- *Color of pubescence.*—156D.
- *Branching habit.*—Basal clumps.

Foliage:
- *Type.*—Evergreen.
- *Shape.*—Ovate.
- *Division.*—Simple.
- *Arrangement.*—Basal leaves are arranged in a whorl, while the leaves on the peduncle are cauline and alternate.
- *Apex.*—Aristulate.
- *Base.*—Attenuate.
- *Venation.*—One prominent mid-vein depressed on adaxial surface and protruding on abaxial surface.
- *Vein color* (*adaxial surfaces*).—138C.
- *Vein color* (*abaxial surfaces*).—138C.
- *Margins.*—Entire.
- *Leaf surface.*—Sinuous.
- *Texture.*—Velutinous particularly on abaxial surface.
- *Basal leaf attachment.*—Petiolate.
- *Petiole dimensions.*—3 mm. in width and 3.50 cm. in length.
- *Petiole surface.*—Pubescent.
- *Petiole color.*—Adaxial surface is 144A and abaxial surface is 144B.
- *Petiole shape.*—Sulcate.
- *Leaf dimensions.*—3.5–7 cm. in length and 2–6 cm. in width on plant in 4-litre container.
- *Leaf color* (*adaxial surface*).—147A with dappled spots that are 148D.
- *Leaf color* (*abaxial surface*).—148B.

Flowers:
- *Inflorescence.*—Cluster of flowers.
- *Quantity of flowers per inflorescence.*—9 to 13 flowers per inflorescence.
- *Flower shape.*—Disc or saucer shaped.
- *Flower dimensions.*—2 cm. in diameter, 9 mm. in depth and 2 cm. in height.
- *Color of corolla tube*—155A.
- *Persistent or self-cleaning.*—Persistent.
- *Aspect.*—Facing upward.
- *Sexuality.*—Bisexual.
- *Bud dimensions.*—0.75 cm. in width and 1.20 cm. in length.
- *Bud shape.*—Obovate.
- *Bud color.*—63B.
- *Flower color.*—63B fading to 64D, then fading to 76C. The flowers also have tints of violet-blue that range from 100B to 100D. All colors are present on an individual plant.
- *Petals*—Six in number.
- *Fused or unfused.*—Fused.
- *Petal margin.*—Entire.
- *Petal surface.*—Glabrous.
- *Calyx dimensions.*—12 mm. in height and 6 mm. in diameter.
- *Calyx surface.*—Pubescent.
- *Calyx color.*—137D.
- *Sepals.*—Six in number.
- *Sepals fused or unfused.*—Fused.
- *Sepal color.*—137D.
- *Sepal surface.*—Pubescent.
- *Sepal apex*—Aristiculate.
- *Peduncle dimensions.*—6 cm. in length and 2 mm. in diameter.
- *Pedicel dimensions.*—1 cm. in length and 1 mm. in width.
- *Peduncle color*—137D.
- *Pedicel color.*—137D.
- *Pedicel surface.*—Pubescent.
- *Peduncle surface.*—Pubescent.

Reproductive organs:

*Stamens.*—Six adnate to corolla wall.

*Stamen color.*—155B.

*Stamen dimensions.*—6.0 mm. in length and 0.50 mm. in diameter.

*Anther color.*—199A.

*Anther dimensions.*—1 mm. in height and 0.50 mm. in width.

*Pistil.*—One.

*Pistil dimensions.*—12 mm. in length and 0.50 mm. in width.

*Pistil color.*—158A.

*Pistil shape.*—Columnar.

*Style color.*—158A.

*Stigma shape.*—Bifid.

*Stigma color*—158A.

*Ovary position.*—Inferior.

*Ovary color.*—143C.

*Ovary shape.*—Round.

*Ovary dimensions.*—3 mm. in height and 3 mm. in diameter.

Seed production: Seed production has not been observed to date.

We claim:

1. A new and distinct cultivar of Pulmonaria plant named 'Pink Haze' as described and illustrated.

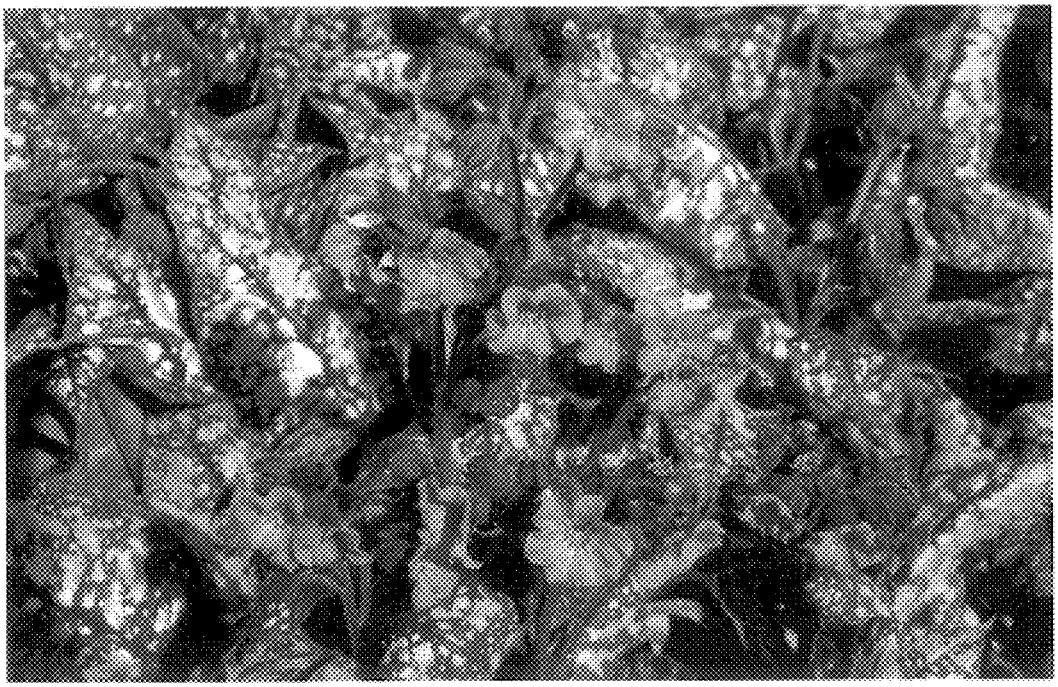

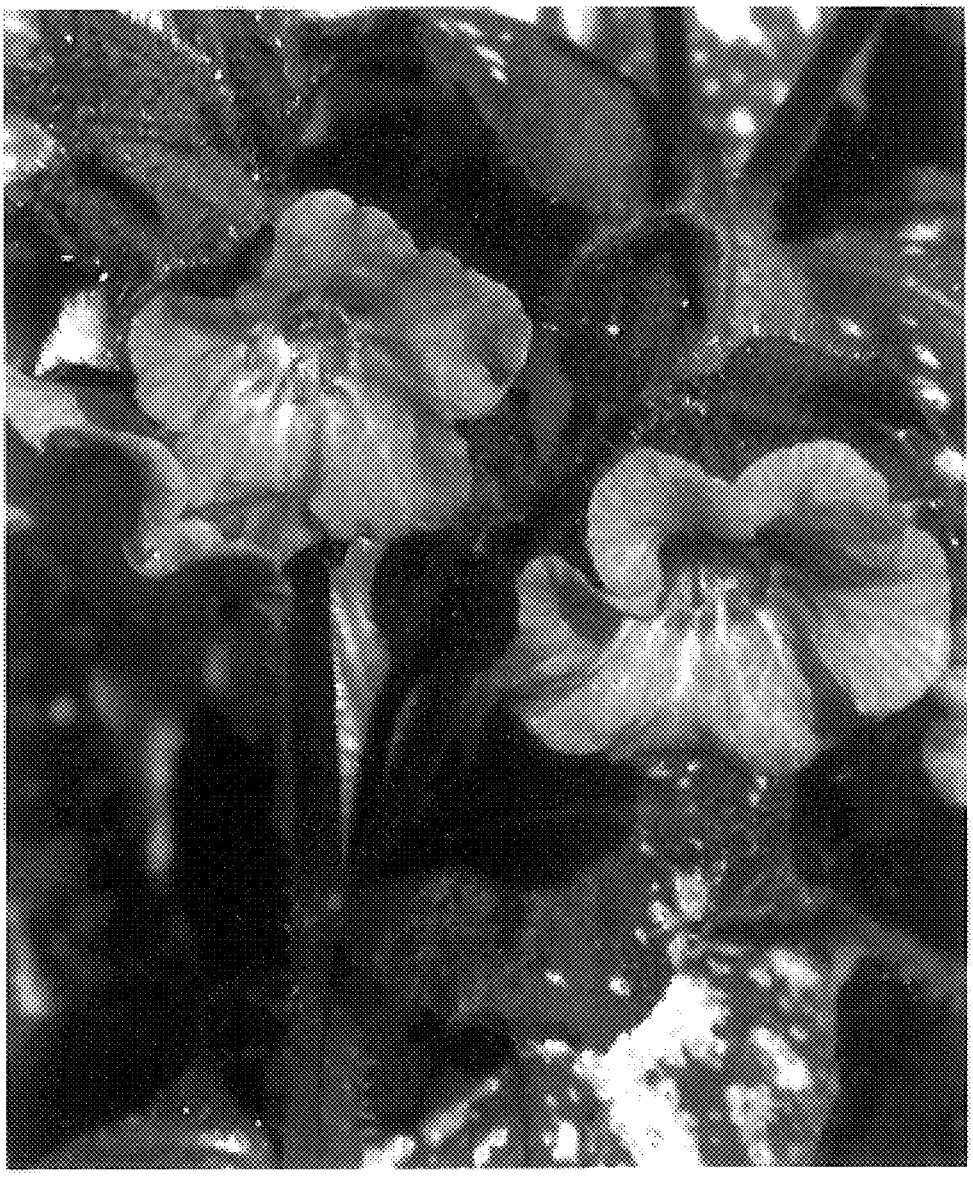

* * * * *